(12) United States Patent
Epstein et al.

(10) Patent No.: US 12,258,421 B2
(45) Date of Patent: *Mar. 25, 2025

(54) HUMANIZED ANTI-NUCLEAR ANTIBODIES FOR TARGETING NECROSIS IN CANCER THERAPY

(71) Applicant: Cancer Therapeutics Laboratories, Inc., Los Angeles, CA (US)

(72) Inventors: Alan Epstein, Los Angeles, CA (US); Peisheng Hu, Los Angeles, CA (US)

(73) Assignee: CANCER THERAPEUTICS LABORATORIES, INC., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/839,953

(22) Filed: Jun. 14, 2022

(65) Prior Publication Data
US 2023/0027730 A1    Jan. 26, 2023

Related U.S. Application Data

(62) Division of application No. 16/496,177, filed as application No. PCT/US2018/023123 on Mar. 19, 2018, now Pat. No. 11,384,157.

(Continued)

(51) Int. Cl.
| | |
|---|---|
| A61K 39/395 | (2006.01) |
| A61K 39/00 | (2006.01) |
| A61K 47/68 | (2017.01) |
| A61K 51/10 | (2006.01) |
| A61P 31/18 | (2006.01) |

(Continued)

(52) U.S. Cl.
CPC ............. *C07K 16/44* (2013.01); *A61K 39/00* (2013.01); *A61K 47/6801* (2017.08); *A61K 51/10* (2013.01); *C07K 16/005* (2013.01); *C12N 15/1058* (2013.01); *C07K 2317/24* (2013.01); *C07K 2317/565* (2013.01);
(Continued)

(58) Field of Classification Search
None
See application file for complete search history.

(56) References Cited

U.S. PATENT DOCUMENTS

| | | |
|---|---|---|
| 2013/0115674 A1 | 5/2013 | Sutkowski et al. |
| 2016/0235859 A1 | 8/2016 | Weisbart et al. |
| 2018/0200366 A1 | 7/2018 | Wong et al. |

FOREIGN PATENT DOCUMENTS

| | | |
|---|---|---|
| WO | 2004/074437 A2 | 9/2004 |
| WO | 2015/106290 A1 | 7/2015 |
| WO | 2017/011411 A1 | 1/2017 |

OTHER PUBLICATIONS

European Patent Office, "Extended European Search Report" dated Dec. 3, 2020, which was issued in connection with related European Patent Application No. 18770253.5 (12 pages).

(Continued)

*Primary Examiner* — Aurora M Fontainhas
(74) *Attorney, Agent, or Firm* — Lucas & Mercanti, LLP

(57) ABSTRACT

Humanized monoclonal anti-nuclear antibodies with enhanced binding affinity and tumor uptake are presented. Particularly preferred antibodies are site-directed mutants of H-CDR3 with up to about 8-fold improvement in affinity as compared to the non-humanized non-mutated form. In further preferred aspects, such humanized antibodies are employed in tumor necrosis targeted delivery of immune modulators, immune effectors, and other therapeutic or diagnostic agents.

17 Claims, 10 Drawing Sheets
Specification includes a Sequence Listing.

Related U.S. Application Data

(60) Provisional application No. 62/473,554, filed on Mar. 20, 2017.

(51) Int. Cl.
    *C07K 16/00*   (2006.01)
    *C07K 16/44*   (2006.01)
    *C12N 5/077*   (2010.01)
    *C12N 15/10*   (2006.01)

(52) U.S. Cl.
    CPC .. *C07K 2317/567* (2013.01); *C07K 2317/622* (2013.01); *C07K 2317/92* (2013.01)

(56) References Cited

OTHER PUBLICATIONS

Hornick, J L; et al., "A new chemically modified chimeric TNT-3 monoclonal antibody directed against DNA for the radioimmunotherapy of solid tumors." Cancer Biotherapy & Radiopharmaceuticals, vol. 13(4), 1998, pp. 255-268.

Hornick, J L; et al., "Single amino acid substitution in the Fc region of chimeric TNT-3 antibody accelerates clearance and improves immunoscintigraphy of solid tumors", Journal of Nuclear Medicine, Society of Nuclear Medicine, vol. 41(2), 2000, pp. 355-362.

ISA/US, PCT International Search Report mailed Aug. 8, 2018 which was issued in connection with the corresponding PCT Application No. PCT/US2018/023123 (11 pages).

Khawli, L A; et al., "Multiple uses of tumor necrosis therapy (TNT) for the treatment and imaging of solid tumors: Preclinical considerations and progress", Update on Cancer Therapeutics, Elselier, vol. 1(1), 2006, pp. 33-47.

Khawli, L A; et al., "Pharmacokinetic characteristics and biodistribution of radioiodinated chimeric TNT-1, -2, and -3 monoclonal antibodies after chemical modification with biotin", Cancer Biother Radiopharm., vol. 17(4), 2002, pp. 359-370.

Shaifi, Jahangir; et al., "Generation of human interferon gamma and tumor Necrosis factor alpha chimeric TNT-3 fusion proteins", Hybrid Hybridomics, vol. 21(6), 2002, pp. 421-432.

Yan, Jianghua; et al., "Humanization and mutation of an antinuclear antibody developed for human cancer therapy", American Association for Cancer Research, Proceedings of the Annual Meeting, American Association for Cancer Research, vol. 43, 2002, p. 910.

FIG. 1A

```
      |---------F1---------|--CDR1--|----F2----|---CDR2---|
            10        20        30        40        50        60        70
mTNT-3/HV   QVQLQQSEAELARPGASVKMSCKASGYTFTRYWMHWVKQRPGQALEWIGAIYPGNSDTSYNQKFKGKAKLT
EP/HV       QVQLVQSGAEVKKPGASVKVSCKASGYTFTRYWMHWVRQAPGQALEWIGAIYPGNSDTSYNQKFKGKATIT
huFd138/HV  QVQLVQSGAEVKKPGASVKVSCKASGYTF_____ WVRQAPGQALEWI_____KATIT
             * *  ***        *                *  *       #                      **

|---------F3---------|---CDR3---|--F4--|
              80        90        100       110       120
mTNT-3/HV   AVTSASTAYMELSSLTSEDSAVYYCARGEEIGVRRWFAYWGQGTLVTVS
EP/HV       ADTSTNTAYMELSSLRSEDTAVYYCARGEEIGVRRWFAYWGQGTLVTVSS
huFd138/HV  ADESTNTAYMELSSLRSEDTAVYFCARG_____WGQGTLVTVSS
             *#  **           *  *    #
```

FIG. 1B

```
      |---------F1---------|--CDR1--|----F2----|-CDR2-|
            10        20        30        40        50        60
mTNT-3/LV   DIVLTQSPATLSVTPGDRVSLSCRARQSINYLHWYQQKSHESPRLLIKYASQSIGIPSRFSGS
EP/LV       EIVLTQSPATLSLSPGERATLSCRARQSINYLHWYQQKPGQAPRLLIYYASQSIGIPDRFSGS
huB-B10/LV  EIVLTQSPATLSLSPGERATLSC_____WYQQKPGQAPRLLIYY____GIPDRFSGS
             *  70  **  80 **        90          100 ****     *      *

|---------F3---------|---CDR3---|--F4--|
mTNT-3/LV   GSGTDFTLSINSVETEDFGMYFCQQSNSWPLTFGAGTKLEIK
EP/LV       GSGTDFTLTISRLEPEDFAVYYCQQSNSWPLTFGQGTKVEIK
huB-B10/LV  GSGTDFTLTISRLEPEDFAVYYCQQSNSWPLTFGQGTKVEIK
             * ***  *   **  *              *  *
```

FIG. 1C

EP/ScFv

| HV | Linker (GSSSS)3 | LV |
|----|----|----|

| EP/ScFv | H-CDR3 Sequence of Master Template |
|---|---|
| | DTAVYYCARG*EGVRRWFAY*WGQGTLVTVSS |
| | ——— H-CDR3 ——— |
| Primers | |
| Pr1 | AVYYCARGEGVRRWFAXWGQGTLV |
| Pr2 | AVYYCARGEGVRRWFXYWGQGTLV |
| Pr3 | AVYYCARGEGVRRWXAYWGQGTLV |
| Pr4 | AVYYCARGEGVRRXFAYWGQGTLV |
| Pr5 | AVYYCARGEGVRXWFAYWGQGTLV |
| Pr6 | AVYYCARGEGVXRWFAYWGQGTLV |
| Pr7 | AVYYCARGEGXRRWFAYWGQGTLV |
| Pr8 | AVYYCARGEXVRRWFAYWGQGTLV |
| Pr9 | AVYYCARGXGVRRWFAYWGQGTLV |
| Pr10 | AVYYCARXEGVRRWFAYWGQGTLV |
| Pr11 | AVYYCAXGEGVRRWFAYWGQGTLV |

FIG. 2

SEQUENCE LISTING

<160> NUMBER OF SEQ ID NOS: 34

<210> SEQ ID NO 1
<211> LENGTH: 6
<212> TYPE: PRT
<213> ORGANISM: Homo sapiens

<400> SEQUENCE: 1

Thr Arg Tyr Trp Met His
1               5

<210> SEQ ID NO 2
<211> LENGTH: 18
<212> TYPE: PRT
<213> ORGANISM: Homo sapiens

<400> SEQUENCE: 2

Gly Ala Ile Tyr Pro Gly Asn Ser Asp Thr Ser Tyr Asn Gln Lys Phe
1               5                   10                  15

Lys Gly

<210> SEQ ID NO 3
<211> LENGTH: 11
<212> TYPE: PRT
<213> ORGANISM: Homo sapiens

<400> SEQUENCE: 3

Glu Glu Ile Gly Val Arg Arg Trp Phe Ala Tyr
1               5                   10

<210> SEQ ID NO 4
<211> LENGTH: 11
<212> TYPE: PRT
<213> ORGANISM: Homo sapiens

<400> SEQUENCE: 4

Arg Ala Arg Gln Ser Ile Ser Asn Tyr Leu His
1               5                   10

<210> SEQ ID NO 5
<211> LENGTH: 6
<212> TYPE: PRT
<213> ORGANISM: Homo sapiens

<400> SEQUENCE: 5

Ala Ser Gln Ser Ile Ser
1               5

<210> SEQ ID NO 6
<211> LENGTH: 9
<212> TYPE: PRT
<213> ORGANISM: Homo sapiens

<400> SEQUENCE: 6

Gln Gln Ser Asn Ser Trp Pro Leu Thr
1               5

<210> SEQ ID NO 7
<211> LENGTH: 121
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala

```
                1               5                  10                 15
            Ser Val Lys Val Ser Cys Lys Ala Ser Gly Tyr Thr Phe Thr Arg Tyr
                        20                  25                 30

Trp Met His Trp Val Arg Gln Ala Pro Gly Gln Ala Leu Glu Trp Ile
                        35                  40                 45

Gly Ala Ile Tyr Pro Gly Asn Ser Asp Thr Ser Tyr Asn Gln Lys Phe
                        50                  55                 60

Lys Gly Lys Ala Thr Ile Thr Ala Asp Thr Ser Thr Asn Thr Ala Tyr
            65                  70                  75                 80

Met Glu Leu Ser Ser Leu Arg Ser Glu Asp Thr Ala Val Tyr Tyr Cys
                        85                  90                 95

Ala Arg Gly Glu Glu Ile Gly Val Arg Arg Trp Phe Ala Tyr Trp Gly
                        100                 105                110

Gln Gly Thr Leu Val Thr Val Ser Ser
                        115                 120

<210> SEQ ID NO 8
<211> LENGTH: 106
<212> TYPE: PRT
<213> ORGANISM: Homo sapiens

<400> SEQUENCE: 8

Ile Val Leu Thr Gln Ser Pro Ala Thr Leu Ser Leu Ser Pro Gly Glu
            1               5                  10                 15

Arg Ala Thr Leu Ser Cys Arg Ala Arg Gln Ser Ile Ser Asn Tyr Leu
                        20                  25                 30

His Trp Tyr Gln Gln Lys Pro Gly Gln Ala Pro Arg Leu Leu Ile Tyr
                        35                  40                 45

Tyr Ala Ser Gln Ser Ile Ser Gly Ile Pro Asp Arg Phe Ser Gly Ser
                        50                  55                 60

Gly Ser Gly Thr Asp Phe Thr Leu Thr Ile Ser Arg Leu Glu Pro Glu
            65                  70                  75                 80

Asp Phe Ala Val Tyr Tyr Cys Gln Gln Ser Asn Ser Trp Pro Leu Thr
                        85                  90                 95

Phe Gly Gln Gly Thr Lys Val Glu Ile Lys
                        100                 105

<210> SEQ ID NO 9
<211> LENGTH: 120
<212> TYPE: PRT
<213> ORGANISM: Homo sapiens

<400> SEQUENCE: 9

Gln Val Gln Leu Gln Gln Ser Glu Ala Glu Leu Ala Arg Pro Gly Ala
            1               5                  10                 15

Ser Val Lys Met Ser Cys Lys Ala Ser Gly Tyr Thr Phe Thr Arg Tyr
                        20                  25                 30

Trp Met His Trp Val Lys Gln Arg Pro Gly Gln Ala Leu Glu Trp Ile
                        35                  40                 45

Gly Ala Ile Tyr Pro Gly Asn Ser Asp Thr Ser Tyr Asn Gln Lys Phe
                        50                  55                 60

Lys Gly Lys Ala Lys Leu Thr Ala Val Thr Ser Ala Ser Thr Ala Tyr
            65                  70                  75                 80

Met Glu Leu Ser Ser Leu Thr Ser Glu Asp Ser Ala Val Tyr Tyr Cys
                        85                  90                 95

Ala Arg Gly Glu Glu Ile Gly Val Arg Arg Trp Phe Ala Tyr Trp Gly
```

```
                100                 105                 110
Gln Gly Thr Leu Val Thr Val Ser
        115                 120

<210> SEQ ID NO 10
<211> LENGTH: 121
<212> TYPE: PRT
<213> ORGANISM: Homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Trp Met His Trp Val Arg Gln Ala Pro Gly Gln Ala Leu Glu Trp Ile
            35                  40                  45

Gly Ala Ile Tyr Pro Gly Asn Ser Asp Thr Ser Tyr Asn Gln Lys Phe
        50                  55                  60

Lys Gly Lys Ala Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Glu Ile Gly Val Arg Arg Trp Phe Ala Tyr Trp Gly
            100                 105                 110

Gln Gly Thr Leu Val Thr Val Ser Ser
        115                 120

<210> SEQ ID NO 11
<211> LENGTH: 121
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Thr Ile His Trp Val Arg Gln Ala Pro Gly Gln Ala Leu Glu Trp Phe
            35                  40                  45

Gly Tyr Ile Tyr Pro Arg Asp Gly His Thr Arg Tyr Ala Glu Lys Phe
        50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Asp Ser Arg Glu Arg Asn Gly Phe Ala Tyr Trp Gly
            100                 105                 110

Gln Gly Thr Leu Val Thr Val Ser Ser
        115                 120

<210> SEQ ID NO 12
<211> LENGTH: 107
<212> TYPE: PRT
<213> ORGANISM: Homo sapiens

<400> SEQUENCE: 12

Asp Ile Val Leu Thr Gln Ser Pro Ala Thr Leu Ser Val Thr Pro Gly
1               5                   10                  15
```

```
Asp Arg Val Ser Leu Ser Cys Arg Ala Arg Gln Ser Ile Ser Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Ile Lys
            100                 105

<210> SEQ ID NO 13
<211> LENGTH: 107
<212> TYPE: PRT
<213> ORGANISM: Homo sapiens

<400> SEQUENCE: 13

Glu Ile Val Leu Thr Gln Ser Pro Ala Thr Leu Ser Leu Ser Pro Gly
  1               5                  10                  15

Glu Arg Ala Thr Leu Ser Cys Arg Ala Arg Gln Ser Ile Ser Asn Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Asn Ser Trp Pro Leu
                 85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Thr Ile Gly Thr Ser
            20                  25                  30

Ile His Trp Tyr Gln Gln Lys Pro Gly Gln Ala Pro Arg Leu Leu Ile
        35                  40                  45

Tyr Tyr Ala Ser Glu Ser Ile Ser Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Ser Ser Ser Trp Pro Leu
                 85                  90                  95

Thr Phe Gly Gln Gly Thr Lys Val Glu Ile Lys
            100                 105

<210> SEQ ID NO 15
```

```
<211> LENGTH: 5
<212> TYPE: PRT
<213> ORGANISM: Artificial Sequence
<220> FEATURE:
<223> OTHER INFORMATION: Linker

<400> SEQUENCE: 15

Gly Ser Ser Ser Ser
1               5

<210> SEQ ID NO 16
<211> LENGTH: 26
<212> TYPE: PRT
<213> ORGANISM: Artificial Sequence
<220> FEATURE:
<223> OTHER INFORMATION: H-CDR3 mutation Primer1
<220> FEATURE:
<221> NAME/KEY: MISC_FEATURE
<222> LOCATION: (19)..(19)
<223> OTHER INFORMATION: Xaa can be any naturally occuring amino acid

<400> SEQUENCE: 16

Ala Val Tyr Tyr Cys Ala Arg Gly Glu Glu Ile Gly Val Arg Arg Trp
1               5                   10                  15

Phe Ala Xaa Trp Gly Gln Gly Thr Leu Val
            20                  25

<210> SEQ ID NO 17
<211> LENGTH: 26
<212> TYPE: PRT
<213> ORGANISM: Artificial Sequence
<220> FEATURE:
<223> OTHER INFORMATION: H-CDR3 mutation primer 2
<220> FEATURE:
<221> NAME/KEY: MISC_FEATURE
<222> LOCATION: (18)..(18)
<223> OTHER INFORMATION: Xaa can be any naturally occuring amino acid

<400> SEQUENCE: 17

Ala Val Tyr Tyr Cys Ala Arg Gly Glu Glu Ile Gly Val Arg Arg Trp
1               5                   10                  15

Phe Xaa Tyr Trp Gly Gln Gly Thr Leu Val
            20                  25

<210> SEQ ID NO 18
<211> LENGTH: 26
<212> TYPE: PRT
<213> ORGANISM: Artificial Sequence
<220> FEATURE:
<223> OTHER INFORMATION: H-CDR3 mutation promer 3
<220> FEATURE:
<221> NAME/KEY: MISC_FEATURE
<222> LOCATION: (17)..(17)
<223> OTHER INFORMATION: Xaa can be any naturally occuring amino acid

<400> SEQUENCE: 18

Ala Val Tyr Tyr Cys Ala Arg Gly Glu Glu Ile Gly Val Arg Arg Trp
1               5                   10                  15

Xaa Ala Tyr Trp Gly Gln Gly Thr Leu Val
            20                  25

<210> SEQ ID NO 19
<211> LENGTH: 26
<212> TYPE: PRT
<213> ORGANISM: Artificial Sequence
<220> FEATURE:
<223> OTHER INFORMATION: H-CDR3 mutation primer 4
<220> FEATURE:
```

```
<221> NAME/KEY: MISC_FEATURE
<222> LOCATION: (16)..(16)
<223> OTHER INFORMATION: Xaa can be any naturally occuring amino acid

<400> SEQUENCE: 19

Ala Val Tyr Tyr Cys Ala Arg Gly Glu Glu Ile Gly Val Arg Arg Xaa
1               5                   10                  15

Phe Ala Tyr Trp Gly Gln Gly Thr Leu Val
            20                  25

<210> SEQ ID NO 20
<211> LENGTH: 26
<212> TYPE: PRT
<213> ORGANISM: Artificial Sequence
<220> FEATURE:
<223> OTHER INFORMATION: H-CDR3 mutation primer 5
<220> FEATURE:
<221> NAME/KEY: MISC_FEATURE
<222> LOCATION: (15)..(15)
<223> OTHER INFORMATION: Xaa can be any naturally occuring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 20

Ala Val Tyr Tyr Cys Ala Arg Gly Glu Glu Ile Gly Val Arg Xaa Xaa
1               5                   10                  15

Phe Ala Tyr Trp Gly Gln Gly Thr Leu Val
            20                  25

<210> SEQ ID NO 21
<211> LENGTH: 26
<212> TYPE: PRT
<213> ORGANISM: Artificial Sequence
<220> FEATURE:
<223> OTHER INFORMATION: H-CDR3 mutation primer 6
<220> FEATURE:
<221> NAME/KEY: MISC_FEATURE
<222> LOCATION: (14)..(14)
<223> OTHER INFORMATION: Xaa can be any naturally occuring amino acid

<400> SEQUENCE: 21

Ala Val Tyr Tyr Cys Ala Arg Gly Glu Glu Ile Gly Val Xaa Arg Trp
1               5                   10                  15

Phe Ala Tyr Trp Gly Gln Gly Thr Leu Val
            20                  25

<210> SEQ ID NO 22
<211> LENGTH: 26
<212> TYPE: PRT
<213> ORGANISM: Artificial Sequence
<220> FEATURE:
<223> OTHER INFORMATION: H-CDR3 mutation primer 7
<220> FEATURE:
<221> NAME/KEY: MISC_FEATURE
<222> LOCATION: (13)..(13)
<223> OTHER INFORMATION: Xaa can be any naturally occuring amino acid

<400> SEQUENCE: 22

Ala Val Tyr Tyr Cys Ala Arg Gly Glu Glu Ile Gly Xaa Arg Arg Trp
1               5                   10                  15

Phe Ala Tyr Trp Gly Gln Gly Thr Leu Val
            20                  25

<210> SEQ ID NO 23
<211> LENGTH: 26
```

```
<212> TYPE: PRT
<213> ORGANISM: Artificial Sequence
<220> FEATURE:
<223> OTHER INFORMATION: H-CDR3 mutation primer8
<220> FEATURE:
<221> NAME/KEY: MISC_FEATURE
<222> LOCATION: (12)..(12)
<223> OTHER INFORMATION: Xaa can be any naturally occuring amino acid

<400> SEQUENCE: 23

Ala Val Tyr Tyr Cys Ala Arg Gly Glu Glu Ile Xaa Val Arg Arg Trp
1               5                   10                  15

Phe Ala Tyr Trp Gly Gln Gly Thr Leu Val
            20                  25

<210> SEQ ID NO 24
<211> LENGTH: 26
<212> TYPE: PRT
<213> ORGANISM: Artificial Sequence
<220> FEATURE:
<223> OTHER INFORMATION: H-CDR3 mutation primer 9
<220> FEATURE:
<221> NAME/KEY: MISC_FEATURE
<222> LOCATION: (11)..(11)
<223> OTHER INFORMATION: Xaa can be any naturally occuring amino acid

<400> SEQUENCE: 24

Ala Val Tyr Tyr Cys Ala Arg Gly Glu Glu Xaa Gly Val Arg Arg Trp
1               5                   10                  15

Phe Ala Tyr Trp Gly Gln Gly Thr Leu Val
            20                  25

<210> SEQ ID NO 25
<211> LENGTH: 26
<212> TYPE: PRT
<213> ORGANISM: Artificial Sequence
<220> FEATURE:
<223> OTHER INFORMATION: H-CDR3 mutation primer 10
<220> FEATURE:
<221> NAME/KEY: MISC_FEATURE
<222> LOCATION: (10)..(10)
<223> OTHER INFORMATION: Xaa can be any naturally occuring amino acid

<400> SEQUENCE: 25

Ala Val Tyr Tyr Cys Ala Arg Gly Glu Xaa Ile Gly Val Arg Arg Trp
1               5                   10                  15

Phe Ala Tyr Trp Gly Gln Gly Thr Leu Val
            20                  25

<210> SEQ ID NO 26
<211> LENGTH: 26
<212> TYPE: PRT
<213> ORGANISM: Artificial Sequence
<220> FEATURE:
<223> OTHER INFORMATION: H-CDR3 mutation primer 11
<220> FEATURE:
<221> NAME/KEY: MISC_FEATURE
<222> LOCATION: (9)..(9)
<223> OTHER INFORMATION: Xaa can be any naturally occuring amino acid

<400> SEQUENCE: 26

Ala Val Tyr Tyr Cys Ala Arg Gly Xaa Glu Ile Gly Val Arg Arg Trp
1               5                   10                  15

Phe Ala Tyr Trp Gly Gln Gly Thr Leu Val
            20                  25

<210> SEQ ID NO 27
```

```
<211> LENGTH: 11
<212> TYPE: PRT
<213> ORGANISM: Artificial Sequence
<220> FEATURE:
<223> OTHER INFORMATION: 101 Ile->His point mutant, synthesized

<400> SEQUENCE: 27

Glu Glu His Gly Val Arg Arg Trp Phe Ala Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: 102 Gly->Arg point mutant, synthesized

<400> SEQUENCE: 28

Glu Glu Ile Arg Val Arg Arg Trp Phe Ala Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: 103 Val->Ser point mutant, synthesized

<400> SEQUENCE: 29

Glu Glu Ile Gly Ser Arg Arg Trp Phe Ala Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: 104 Arg->Leu point mutant, synthesized

<400> SEQUENCE: 30

Glu Glu Ile Gly Val Leu Arg Trp Phe Ala Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: 104 Arg->Thr point mutant, synthesized

<400> SEQUENCE: 31

Glu Glu Ile Gly Val Thr Arg Trp Phe Ala Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: 107 Phe->Arg point mutant, synthesized

<400> SEQUENCE: 32

Glu Glu Ile Gly Val Arg Arg Trp Arg Ala Tyr
1               5                   10

<210> SEQ ID NO 33
<211> LENGTH: 11
```

```
<212> TYPE: PRT
<213> ORGANISM: Artificial Sequence
<220> FEATURE:
<223> OTHER INFORMATION: 109 Tyr->Arg, synthesized

<400> SEQUENCE: 33

Glu Glu Ile Gly Val Arg Arg Trp Phe Ala Arg
1               5                   10

<210> SEQ ID NO 34
<211> LENGTH: 11
<212> TYPE: PRT
<213> ORGANISM: Artificial Sequence, synthesized
<220> FEATURE:
<223> OTHER INFORMATION: 109 Tyr->Thr, synthesized

<400> SEQUENCE: 34

Glu Glu Ile Gly Val Arg Arg Trp Phe Ala Thr
1               5                   10
```

HUMANIZED ANTI-NUCLEAR ANTIBODIES FOR TARGETING NECROSIS IN CANCER THERAPY

CROSS-REFERENCE TO RELATED APPLICATIONS

This application is a Divisional of U.S. patent application Ser. No. 16/496,177, filed Sep. 20, 2019, now U.S. Pat. No. 11,384,157, which is a 371 of PCT/US2018/023123, filed Mar. 19, 2018, which in turn claims the benefit of U.S. Provisional Patent Application No. 62/473,554, filed Mar. 20, 2017, the contents of each of which are incorporated herein by reference.

REFERENCE TO A SEQUENCE LISTING SUBMITTED ELECTRONICALLY VIA EFS-WEB

This application contains references to amino acid sequences and/or nucleic acid sequences which have been submitted concurrently herewith as the sequence listing text file entitled: 1023C-1002-W-US-D Substitute-2_ST25; size: 16,735 bytes; and date of creation: Aug. 14, 2024. The aforementioned sequence listing is hereby incorporated by reference in its entirety.

JOINT RESEARCH AGREEMENT

The presently claimed invention was made by one or more parties to a joint research agreement that has been in effect since 18 Apr. 2016. The parties to the agreement are (1) NantCell, Inc. (a Delaware corporation) and (2) Cancer Therapeutics Laboratories, Inc. (a California corporation).

FIELD OF THE INVENTION

The field of the invention is antibodies, and especially humanized antibodies that target necrosis in a tumor.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Previously monoclonal antibodies directed against universal, intracellular antigens that become accessible after cell death have been employed in immunotherapy of solid tumors (see e.g., *Cancer Research*, 48:5842-5848, 1988; *Hybridoma*, 12(6):689-698, 1993; or *Cancer Biotherapy & Radiopharmaceuticals*, 13(4):255-68, 1998). Advantageously, such approach targets necrotic regions of tumors that are present in all tumors but are generally not available in normal tissues of the body. For example, three "tumor necrosis targeting ("TNT") murine monoclonal antibodies have been studied and include muTNT-1 that is directed against histone H1 and DNA, muTNT-2 which binds to a common epitope of histone fractions H1 and H3, and muTNT-3 which principally binds single stranded DNA. Notably, biodistribution analysis in tumor-bearing mice demonstrated that TNT-3 showed the highest uptake in tumor compared to muTNT-1 and muTNT-2, and TNT-3 has been proposed for radioimmunotherapy of solid tumors (see e.g., *Cancer Biother Radiopharm* 1998 August; 13(4):255-68). In an alternative approach, a chimeric TNT-3 antibody/ murine interferon-gamma fusion protein was constructed for the immunotherapy of solid malignancies (see e.g., *Hybrid Hybridomics* 2003 August; 22(4):197-207) and exhibited various desirable characteristics.

Unfortunately, murine monoclonal antibodies are immunogenic in human and therefore have greatly limited therapeutic potential in human patients. To help address issues associated with immunogenicity a chimeric TNT-3 antibody was constructed using human constant regions representing 65% of the molecule and murine variable regions. However, as such chimeric antibody still contained about 35% murine residues, the antibody remained immunogenic.

To further reduce immunogenicity of chimeric antibodies, various approaches can be undertaken. One of the simplest humanization approaches is complementarity-determining region (CDR) grafting in which the six antibody CDRs are simply grafted into corresponding human framework regions, which further reduces the number of murine residues by about 25%. Unfortunately, while CDR grafting has, at least in some cases, been successfully used in humanization of several antibodies, grafting often changes the binding profiles, resulting in an undesirable decrease in affinity to the antigen (see e.g., *J Mol Biol* 224:487-499, 1992), up to several hundred fold as reported elsewhere (see e.g., *Proc. Natl Acad. Sci. USA*, 89(10):4285-9, 1992). Therefore, in most cases, CDR grafting must be combined with fine turning of some framework residues that are potentially important to restore the affinity of humanized antibodies. However, the number of important framework residues that can potentially contribute to CDR structure is relatively large and often precludes a rationale-based antibody design. Moreover, interactions between framework residues and one or more CDRs further complicate the analysis, rendering fine-tuning methods generally time-consuming and unpredictable.

In yet another approach, the affinity of a humanized antibody was restored by step-wise mutations of the CDRs (see e.g., *Proc. Natl Acad. Sci. USA*, 95, 6037-6042, 1998). Still others reported that the diversity in the CDR region of the VH chain was sufficient for most antibody specificities and pointed out that somatic mutations can allow for surprisingly high affinities. Indeed, H-CDR3 was shown to play a dominant role in antigen binding as was suggested by earlier studies, showing that a heavy chain alone or even single VH domains can bind antigens with a comparable affinity as the intact antibody (see e.g., *Nature* 341, 544-546, 1989; and *J. Immunol. Methods* 193, 177-187, 1996). Of course, modifications of selected CDRs may once more lead to changes in overall configuration of the binding site, leading yet again to a high level of unpredictability.

Thus, there remains a need for humanized antibody compositions and methods that allow targeting of a tumor microenvironment, and especially necrotic cells, to allow for site-specific modulation of immune response to a tumor.

SUMMARY OF THE INVENTION

The inventive subject matter is directed to compositions and methods of generating and use of humanized TNT antibodies with improved binding characteristics.

In one aspect of the inventive subject matter, the inventors contemplate a humanized anti-nuclear antibody having an improved binding affinity to a nuclear target (e.g., DNA, especially single stranded DNA (ssDNA)) relative to a corresponding non-humanized antibody. Especially contemplated humanized antibodies have a binding affinity that is at least 2-fold, more typically at least 4-fold, and most typically at least 8-fold higher than the corresponding non-humanized antibody. Moreover, preferred humanized antibody have a mutated amino acid in H-CDR3 relative to the corresponding non-humanized antibody. For example, the mutated amino acid in H-CDR3 may be 107Phe→Arg, 101Ile→His, 102Gly→Arg, 109Tyr→Thr, 103Val→Ser, 104Arg→Thr, 109Tyr→Arg, and 104Arg→Leu.

Viewed from a different perspective, the humanized antibody may have at least one of an H-CDR1 sequence comprising TRYWMH (SEQ ID NO:1), an H-CDR2 sequence comprising GAIYPGNSDTSYNQKFKG (SEQ ID NO: 2), an H-CDR3 sequence comprising EEIGVRRW-FAY (SEQ ID NO: 3), an L-CDR1 sequence comprising RARQSISNYLH (SEQ ID NO: 4), an L-CDR2 sequence comprising ASQSIS (SEQ ID NO: 5), and an L-CDR3 sequence comprising QQSNSWPLT (SEQ ID NO: 6). Therefore, in still further contemplated aspects, the humanized antibody may have a VH sequence comprising: QVQLVQSGAEVKKPGASVKVSCK-ASGYTFTRYWMHWVRQAPGQALEWIGAIYPGNSD TSYNQKFKGKATITADTSTNTAYMELSSLRSED-TAVYYCARGEEIGVRRWFAYWGQGT LVTVSS (SEQ ID NO: 7), and/or a VL sequence comprising IVLTQSPATLSLSPGERATLSCRARQSIS-NYLHWYQQKPGQAPR LLIYYASQSIS-GIPDRFSGSGSGTDFTLTISRLEPEDFAVYYCQQSN-SWPLTFGQGTKVEIK (SEQ ID NO: 8).

In another aspect of the inventive subject matter, the inventors also contemplate a hybrid molecule that includes at least a binding portion of the humanized antibody contemplated herein that is coupled to a therapeutic agent and/or an imaging agent. For example, suitable binding portions of the antibody include full length antibodies, Fab fragments, F(ab')$_2$ fragments, Fab$_2$ fragments, and scFvs, while contemplated therapeutic agent include a cytokine or portion thereof, a chemokine or portion thereof, an inhibitor of a myeloid-derived suppressor cell (MDSC), an inhibitor of an M2 macrophage, a radioisotope, a co-stimulatory molecule, a toll-like receptor ("TLR") agonist or ligand, a molecule interfering with epithelial mesenchymal transition ("EMT"), and/or a chemotherapeutic drug. Contemplated imaging agents include radioisotopes, positron emission tomography (PET) labels, and/or single-photon emission computed tomography (SPECT) labels. Therefore, the inventors also contemplate pharmaceutical compositions that comprise an antibody or a hybrid molecule as presented herein. Most typically, such pharmaceutical compositions will be formulated for injection.

In yet another aspect of the inventive subject matter, the inventors contemplate methods of targeting a necrotic cell, wherein such methods will include a step of contacting the necrotic cell with an antibody or hybrid molecule as presented herein. While not limiting to the inventive subject matter, it is typically preferred that the necrotic cell is a necrotic tumor cell in a tumor microenvironment, and/or that the step of contacting is performed in vivo.

Thus, the inventors also contemplate a method of delivering a therapeutic or imaging agent to a tumor microenvironment containing necrotic tumor cells. In such method a therapeutic or imaging agent is provided that is coupled to an antibody as presented herein. The necrotic tumor cells are then contacted in the microenvironment with the therapeutic or imaging agent under conditions that allow the antibody to bind to a nuclear target in the necrotic cell in the tumor microenvironment.

In preferred aspects, the therapeutic agent comprises at least one of a cytokine or portion thereof, a chemokine or portion thereof, an inhibitor of an MDSC, an inhibitor of an M2 macrophage, a radioisotope, a co-stimulatory molecule, a TLR agonist or ligand, a molecule interfering with EMT, and a chemotherapeutic drug, while the imaging agent comprises at least one of a radioisotope, a PET label, and a SPECT label. Most typically, the tumor is a solid tumor, and delivery of the therapeutic or imaging agent may be enhanced using a vasculature permeability enhancing agent (e.g., IL-2).

In still further aspects of the inventive subject matter, the inventors further contemplate method of producing an affinity optimized humanized antibody from a murine antibody. Most typically, such method will include a step of identifying a human antibody sequence having a predetermined minimum identity (e.g., at least 90%, or 92%, or 94%, or 96%, excluding CDRs) with the murine antibody sequence. In another step, the murine CDRs for VH and VL are grafted into respective VH and VL of the identified human antibody sequence to so obtain chimeric VH and VL sequences, and a scFv-hybrid is generated using the chimeric VH and VL sequences. Site-directed mutagenesis is then performed in H-CDR3 to generate a scFv-hybrid library, and affinity selection (and/or maturation) is used to identify a binder from the scFv-hybrid library. In yet another step, the chimeric VH and VL sequences of the binder are grafted into the human antibody sequence to so obtain the affinity optimized humanized antibody.

Most typically, the scFv-hybrid is a phage display hybrid, but may also be an RNA display hybrid. Moreover, it is generally preferred (but not necessary) that the site-directed mutagenesis in H-CDR3 is directed against a single amino acid position of the H-CDR3. Likewise, it is preferred (but not necessary) that the affinity selection is performed over at least three successive selection/enrichment cycles. Where desired, the affinity selection may further include at least one step of additional site-directed mutagenesis in H-CDR3 and/or a framework region.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 1A, 1B and 1C provide schematics illustrating an exemplary alignment of VH (FIG. 1A) and VL (FIG. 1B) sequences of human, murine, and humanized protein portions, and a general assembly of an exemplary EP/scFv (FIG. 1C). In FIG. 1A, mTNT-3/HV is SEQ ID NO: 9; EP/HV is SEQ ID NO: 10, and HuFd138/HV is SEQ ID NO: 11. In FIG. 1B, mTNT/LV is SEQ ID NO: 12, EP/LV is SEQ ID NO: 13 and huB-B10/LV is SEQ ID NO: 14.

FIG. 2 illustrates the mutation of H-CDR3 of EP/ScFv and panning of its library against crude DNA. The EEIGVRRWFAY (SEQ ID NO: 3) domain is the heavy chain CDR3 sequence. The shaded "X" can be any one of the 20 naturally occurring amino acids. Primers Pr1 through Pr11 are SEQ ID NOs: 16 through 26, respectively.

DETAILED DESCRIPTION

Figure 3:
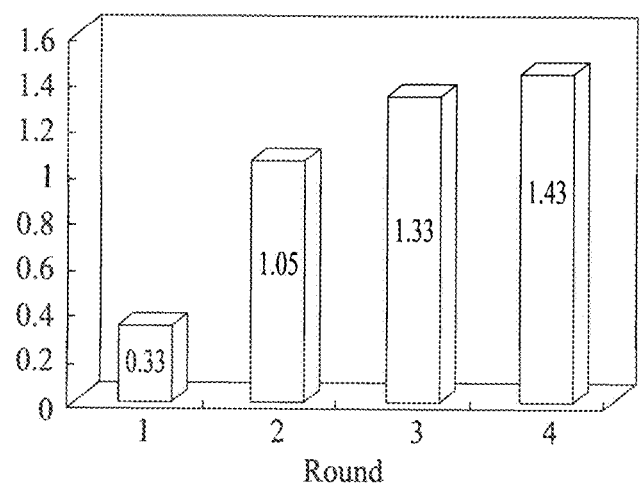
FIG. 3 is a graph depicting exemplary increases in binding over successive rounds of panning.

The inventors have now discovered that antibodies against various targets can not only be humanized but also improved with respect to their antigen affinity in a conceptually simple and effective manner. For example, and as is described in more detail below, the inventors converted a murine anti-nuclear antibody into a humanized antibody with substantially improved affinity.

More particularly, and based on a desired murine antibody (e.g., murine antibody binding to ssDNA) corresponding human antibody sequences were identified in antibody databases that had highest amino acid identity. Most typically, suitable human antibody sequences will have a predetermined minimum identity of at least 90%, or at least 92%, or at least 94%, or at least 96%, excluding CDRs. Once identified, the murine CDRs for VH and VL are then grafted into the human sequences to thereby obtain chimeric VH and VL sequences, using conventional methods well known in the art. Of course, it should be appreciated that such grafting step can be done in vitro or in silico where the actual chimeric sequences are not needed for experimentation. Regardless of the manner of grafting, a scFv-hybrid is then generated using the chimeric VH and VL sequences as a base structure for affinity maturation or other improvement as needed. Once more, there are numerous methods of making scFv from actual nucleic acid portions or sequence information known in the art, and all manners of generating such scFv are deemed suitable for use herein. In especially preferred aspects, the scFv is fused to a selection system that allows for rapid identification and clonal amplification of variants with desired affinity or other molecular property. For example, selection systems appropriate for use herein include various phage panning systems (e.g., based on pIII, pVIII, pIX) and RNA display systems (e.g., puromycin linkage based), and it should be appreciated that all known manners of affinity maturation and isolation of selected closes are deemed suitable for use herein. Therefore, clonal selection and/or affinity maturation may include one or more steps of intermittent site-directed mutagenesis that targets at least one of the CDRs and/or framework regions.

In further aspects of the inventive subject matter, the inventors noted that affinity and even bioavailability/uptake could be improved by modifying only the H-CDR3 portion. Notably, the inventors performed single amino acid scanning and discovered that selected mutants had substantially increased binding as is also shown in more detail below. Advantageously, such mutagenesis can be done using scFv format rather than testing the full length antibody (typically IgG). As will be readily appreciated, the affinity improved chimeric VH and VL sequences of the scFvs can then be grafted into the human antibody sequence to so obtain the affinity optimized humanized antibody. Prepared humanized and affinity improved anti-nuclear antibodies were then tested in various assays to confirm proper and selective binding as is also shown in more detail below.

With respect to contemplated uses of thusly prepared antibodies it should be appreciated that the anti-nuclear antibodies presented herein are particularly beneficial in targeting necrosis, and especially necrotic cells in a tumor microenvironment. As the tumor microenvironment is often a difficult-to-target environment that promotes various mechanisms of immune evasion (e.g., hypoxia reducing activity of NK cells, lack of nutrients and oxygen promoting EMT, etc.), specific delivery and retention of various immune stimulating factors to the microenvironment is thought to particularly benefit immune therapy.

In that regard, it should be appreciated that the terms 'apoptosis' and 'necrosis' are not interchangeably used herein, but refer to two principally distinct mechanisms and pathways of cell death. While apoptosis is a well-defined process of programmed cell death involving specialized signaling events and staged cell shut-down (e.g., blebbing, cell shrinkage, nuclear fragmentation, chromatin condensation, DNA fragmentation, mRNA decay), necrosis is typically evidenced as a disorganized process of cell death with concomitant loss of organelle function, cell rupture, and release of cell content into the environment. Furthermore, necrosis is typically accompanied by an inflammatory cell response. Moreover, it should be appreciated that necrosis is the site by which the immune system "sees" the tumor and reacts immunologically. This is important since delivering payloads to necrosis will aid the immune system in recognizing and reacting to a tumor, and thus is the preferred site of delivery of these therapeutically effective payloads.

The inventors therefore also contemplate the use of the antibodies and fragments thereof to deliver an imaging and/or therapeutic agent to the tumor microenvironment. Most typically, the antibody, or fragment thereof will have specific binding (i.e., binds with a Kd of less than $10^{-7}$ M, and more typically less than $10^{-8}$ M as, for example, determined by Surface Plasmon Resonance (SPR) or other technique) to the nuclear target, and especially ssDNA. Most typically (but not necessarily in all cases), the binding to ssDNA will be independently of the presence of histones and other nucleoproteins.

Of course, it should be appreciated that the imaging and/or therapeutic agent may be coupled to the antibody (or fragment thereof) in numerous manners, including covalent and non-covalent binding. Most typically, the coupling will be covalent coupling, which may be achieved using conventional coupling chemistry such as amino group reactive reagents (e.g., N-hydroxy-succinimide esters, various aldehydes, carbodiimide compounds, epoxides, imidoesters, etc.), or sulfhydryl group reactive reagents (e.g., various maleimides, thiols, etc.), or may be implemented via recombinant cloning techniques in which the antibody (fragment) is fused in frame to an optional linker that is fused in frame to the second protein of interest. Suitable linkers may be selected by a desired length (e.g., to provide a desired spatial distance), amino acid composition (e.g., to provide a cleavable linker or flexible linker), etc. In still further contemplated modes of coupling, coupling may be non-covalently and in especially preferred manners, the coupling is provided by elements of known binding pairs, such as biotin/avidin, cellulose/cellulose binding protein, nickel-nitrilotriacetic acid (Ni-NTA)/oligo-histidyl, etc.

With respect to diagnostic agents, it is contemplated that all detectable (and preferably quantitatively detectable) agents are deemed suitable for use herein. Furthermore, it should be noted that the detection may be performed ex vivo (e.g., on tissue section) and/or in vivo using suitable methods known in the art. For example, visually detectable imaging agents include fluorophores, luminescent groups, catalytically active groups (e.g., to precipitate a dye and/or activate a chromogen or luminogen), radiographically detectable groups (e.g., PET, SPECT, NMR label, radioisotope, etc.).

Likewise, and with respect to therapeutic agents, it is contemplated that all therapeutic agents are deemed appropriate for use herein. However, in particularly preferred aspects of the inventive subject matter, the therapeutic agent will have an immune stimulatory effect. Most typically, such stimulator effect will reverse or neutralize one or more mechanisms that lead to immune evasion of cancer cells in the tumor microenvironment. For example, where the immune evasion is based on the recruitment of M2 macrophages or regulatory T-cells (Tregs), suitable therapeutic agents will include those that specifically deactivate or destroy such inhibitory cells (e.g., gemcitabine, RP-182 (see SEQ ID NO: 121 of U.S. Pat. No. 9,492,499), or cyclophosphamide). Additionally, or alternatively, where the immune evasion is based on checkpoint inhibition with effector and/or helper cells, binders or antagonists to CTLA4 or PD1 (e.g., ipilimumab, pembrolizumab, etc.) are contemplated.

Conversely, it should also be appreciated that an immune therapy may be enhanced by use of a therapeutic agent where the therapeutic agent has immune stimulatory activity. Such immune stimulatory activity can be achieved via use of co-stimulatory signals that are coupled to the antibody or fragment thereof, preferably in the context of one or more tumor (neo)antigens. For example, co-stimulatory signals include 4-1BBL, OX40L, GITRL, TIM3, LFA3, ICAM1, ICOSL, etc. In addition, it should be appreciated that immune stimulatory agents will also include immune stimulating cytokines such as IL-2, IL-12, IL15, IL-15 superagonists, TLR agonists and ligands, etc. Still further, it should be appreciated that the therapeutic agent may also comprise a (pro-inflammatory) chemokine that will attract further immune competent cells. In this context, it should be appreciated that the therapeutic agents will typically not kill tumor cells at the site of necrosis (as necrotic cells are already non-viable), but promote an enhanced immune reaction against tumor cells proximal to the necrotic tissue (e.g., taking advantage of antigen spread and antigen cascading, or by reversal of immune suppressive mechanisms).

Where desired, the therapeutic agent may also include agents that will target factors that contribute to EMT (epithelial mesenchymal transition) in the tumor microenvironment, including IL-8 and TGF-β. Therefore, suitable therapeutic agents will also include those that bind or otherwise sequester IL-8 and TGF-β (e.g., a TGF-β receptor).

Additionally, the therapeutic agent may also include more conventional drugs used in the treatment of cancer. For example, typical anticancer drugs include antimetabolites, drugs that interfere with microtubule formation or disassembly, DNA alkylating agents, and topoisomerase inhibitors, cytotoxic drugs, etc., all of which may be cleavable under conditions prevalent in the tumor microenvironment. Contemplated therapeutic agents also include radiotherapeutic agents such as alpha and beta emitters (e.g., Bi-213, Pb-212, I-131, Ac-225, Sr-89, etc.). Such agents will generally affect non-necrotic tumor cells within the tumor or tumor microenvironment.

Consequently, and as is shown in more detail below, the inventors generally contemplate a method of targeting a necrotic cell (typically a tumor cell, most typically a necrotic tumor cell in a tumor microenvironment) that includes a step of contacting the necrotic cell with a binding agent that specifically binds to a nuclear target, and especially ssDNA. Moreover, the contacting can be performed in such methods in vivo or in vitro. For example, where the step is performed in vitro, relatively small quantities (e.g., between 0.001-100 μg, or between 0.01-0.1 μg, or between 0.001-0.01 μg) of the antibody may be required. On the other hand, where the step is performed in vivo, relatively large quantities (e.g., between 0.01-100 mg, or between 0.1-10 mg, or between 1-10 mg) of the antibody may be required. Of course, it should be appreciated that where the antibody is coupled to an imaging and/or therapeutic agent, the quantity of the antibody will also be at least in part determined by the type and quantity of the imaging and/or therapeutic agent needed for the desired effect.

Consequently, the inventor also contemplates a method of delivering a therapeutic and/or imaging agent to a tumor microenvironment containing necrotic tumor cells. As noted above, such method will typically include a step of providing a therapeutic or imaging agent that is coupled to the antibody that binds to a nuclear target (and especially ssDNA), and a further step of contacting (preferably in vivo) the necrotic tumor cells in the microenvironment with the therapeutic or imaging agent under conditions that allow the antibody to bind to the nuclear target in the necrotic cell in the tumor microenvironment.

In addition, the methods contemplated herein may further include one or more steps of increasing tumor necrosis to thereby enhance uptake of the modified antibody into the tumor to so optimize the delivery of a therapeutic or diagnostic payload. For example, suitable further steps include radiotherapy, chemotherapy, or immunotherapy, and especially low-dose metronomic chemotherapy and radiotherapy.

EXAMPLES

Reagents: The plasmids pEE6hCMV-B and pEE12 with the Glutamine Synthetase Gene Amplification System were purchased from Lonza Biologics (Slough, UK). Restriction endonucleases, T4 DNA ligase, and other molecular biology reagents were purchased from New England Biolabs (Beverly, MA) or Boehringer Mannheim (Indianapolis, IN). RPMI-1640 medium, MEM non-essential amino acids solution, penicillin-streptomycin solution, degraded crude DNA, ABTS (2,2'-azobenzene-2-carboxylic acid) were purchased from Sigma Chemical Co. (St. Louis, MO). Hybridoma serum free medium (SFM medium), with and without glutamine, was purchased from Life Technologies, Inc. (Gaithersburg, MD) and dialyzed fetal bovine serum was obtained from HyClone Laboratories, Inc. (Logan, UT). Iodine-125 was obtained as sodium iodide in 0.1N sodium hydroxide from DuPont/New England Nuclear (North Billerica, MA). Six-week-old BALB/c mice were purchased from Harlan-Sprague Dawley (Indianapolis, IN).

Design and Assembling of EP/ScFv: By searching human antibody databases, two sequences, huFd138 HV and hu B-B10 LV, had the most identity to the original TNT-3 amino acid sequence of heavy chain and light chain, respectively. Because of this, they were used as master templates to construct the EP variable heavy and light chains, respectively. Six CDRs were then simply grafted into corresponding human framework regions. The six murine TNT-3 CDR sequences were converted into the corresponding nucleotide sequences using the codon-usage observed in the known human antibodies. Variable heavy and light chain sequences were combined with a (GSSSS)3 linker to construct the EP/ScFv. The designed DNA sequences were divided into eight overlapping oligonucleotides and synthesized.

A full-length ScFv was obtained by a serial assembling PCR and amplified with a pair of primers at 5' and 3' ends. The PCR products digested with NotI and SpeI were cloned into pBlueScript SK(–). By DNA sequencing, one clone with the correct sequence was selected as the standard template for the next mutation. To restore and improve the affinity of EP antibody candidates (also referred to herein as EP or huTNT IgG1 or antibodies), a site-specific random mutation on the H-CDR3 domain, which covers 11 codons, was performed. A set of primers that contained 11 site-specific mutations was designed. Using PCR, random mutation of 11 amino residues was introduced step by step. The 11 mutated and humanized ScFvs were amplified by PCR with a pair of primers at 5' and 3' end. The PCR products were then purified and digested with NotI and SpeI, and inserted into a digested lambda phage SurfZAP™ vector. Packaged SurfZAP™ vector infected host cells XL-1 were then amplified and excised into phagemid pSurfscript™ SK(–) with ExAssist™ help phage. Phagemids grew in SOLR cells to eliminate help phage and were amplified in XL-1 cells. EP/ScFv were expressed as fusion proteins (ScFv/cpIII) and allowed to incorporate into the coat protein of recombinant phagemid particles with VCSM13 helper phage. Phagemids were recovered and concentrated from the Amplified supernatant by PEG precipitation.

Four rounds of biopanning against crude DNA coated onto 25 ml flasks were conducted according to the STRATA-GENE protocol. Briefly, for each panning, >$10^{12}$ phagemids in 3 ml PBS were used. Unbound phage was removed with 10 PBST washes, and bound phages were eluted with 5 ml glycine-HCl (pH 2.2). The titer of eluted phage was determined by plating 100 µl of the infected bacteria onto selective plates in order to count colony forming units (c.f.u.). ScFv phage from the fourth round of panning were tested for reactivity with crude DNA by phage-ELISA with 100 µl of 10 µg/ml crude DNA coated to each well of the ELISA plate. Bound phage were detected with rabbit anti-M13 antibody, following by goat anti-rabbit antibody horseradish peroxidase conjugate. A405 values were determined after incubation with substrate (ABTS) for 10 min and were measured by ELISA reader.

Construction and Expression of EP IgG: To restore the intact antibody molecule, EP/ScFv was converted into EP IgG1. To accomplish this, the variable regions of EP heavy and light chains were PCR-amplified from the cloning vectors using primers designed to introduce appropriate restriction endonuclease sites. The heavy chain variable region was introduced into the expression vector pEE6hCMV-B into which the human Gamma 1 constant region (CH) was previously cloned. The light chain variable region was inserted into the expression vector pEE12 that contained the human VL constant region cDNA. The final expression vectors were pEE6hCMV-B/EP HC and pEE12/EP LC, containing transcription cassettes for the human light and heavy chains, respectively, each under the control of the CMV major immediate early promoter. pEE12/EP LC also contains the cDNA sequence for the selectable marker glutamine synthetase, under the control of the SV40 early promoter. After completing each vector, the pEE6hCMV-B/EP HC and pEE12/EP LC vectors were co-transfected into host NS0 murine myeloma cells for the expression of EP IgG1. Supernatants containing the antibody products were initially identified by indirect ELISA using 96 well microtiter plates coated with degraded crude DNA at 10m/ml. The highest producing clone was identified by a 24 hour rate of production assay. After two rounds of subcloning by limiting dilution, the highest producing clone was expanded and EP IgG1 was purified stepwise from the cell culture supernatant by protein A affinity chromatography and ion-exchange chromatography. The purity of the EP antibodies was examined by SDS-PAGE.

Determination of Crude DNA Binding by ELISA: To measure DNA binding activities of the EP IgG candidates, 96-well ELISA plates were coated with 100 µl of 10 ug/ml crude DNA and blocked with 1% BSA-PBS, serial dilution of the EP IgG candidates were added into wells and incubated at 37° C. for 1 hour. The purified chTNT-3 was used as the standard. Any unbound antibodies were removed using triplicate wash with 0.05% PBST, then goat anti human IgG secondary antibody conjugate horseradish peroxidase was added, followed by chromogenic substrate. $OD_{405}$ was measured by an ELISA reader.

Localization of EP Candidates in Raji Cells by Indirect Immunofluorescence Staining: To observe localization of these EP IgG candidates in Raji cells, indirect immunofluorescence staining was performed. Briefly, Raji cells were fixed with 10% buffered neutral formalin and washed with PBS. 104 Raji cells in 200 µl PBS reacted to various EP antibodies in 1.5 ml tubes for 1 hour at 37° C. The cells were washed 5 times with PBST and unbound antibody was removed by centrifuge. FITC-conjugated goat anti-human IgG antibody was added in 1:30 dilution, and Raji cells were finally collected in 20 µl PBS and spread onto slides for observation under a fluorescence microscope.

Preparation of Iodine-125 labeled MAbs: Iodine-125 labeled MAbs were prepared using a modified chloramine-T method. Briefly, 1 mCi of $I^{125}$ and 20 µl of an aqueous solution of chloramine-T (2 mg/ml) were added to a 5-ml test tube containing 100 µg MAb in 100 µl PBS. The solution was quenched after 2 min with 10 µl of an aqueous solution of sodium metabisulfite. Each reaction mixture was then purified using a Sephadex G-25 column which typically yielded a 90%-95% recovery. The radiolabeled MAbs were diluted with PBS for injection, stored at 4° C., and administered within 2 h after labeling.

Binding and Biodistribution Studies: The in vitro immunoreactivities of the radiolabeled MAbs were evaluated by a conventional fixed cell radioimmunoassay using Raji cells. Briefly, radioiodinated MAbs (approximately 100,000 cpm/tube) were incubated in triplicate with $10^6$ fixed Raji cells for 1h with intermittent mixing. Following incubation, the cells were washed 3× with 1% BSA in PBS. Bound MAb was detected by measuring the cell pellet-associated radioactivity in a gamma counter. To determine the avidity constant (Ka) of EP antibodies, the antigen cells, fixed Raji Burkitt's lymphoma cells, were used. Various concentration (10-110 ng) of the $^{125}$I-labeled EP antibodies was incubated with $10^6$ fixed Raji cells at room temperature with constantly mixing, removed unbound radioactivity with 3 time washing of PBST, and then the amount of bound radioactivity was counted in a gamma counter and used to calculate the avidity constant (Ka) by Scatchard analysis. The avidity constant Ka was determined by the K=−(slope/2).

To examine the biodistribution of EP antibody(ies) and chTNT-3, 6-week-old female athymic nude mice were injected with a 0.2 ml inoculum containing $10^7$ LS174T human colon adenocarcinoma cells s.c in the left flank. The tumors were grown until they reached approximately 1 cm in diameter. Within each group (n=5), individual mice were injected i.v. with a 0.1 ml inoculum containing 100 µCi/10 µg of $^{125}$I-labeled MAb. Mice were sacrificed at various times post-injection, and organs, blood, and tumors were removed and weighed. The radioactivity in the samples was then measured and expressed as % ID/g and tumor/organ ratios (cpm per gram tumor/cpm per gram organ). Significance levels were determined using the Wilcox rank sum test.

Design and Construction of Humanized TNT-3/ScFv: To design the humanized TNT-3 frameworks of V region, the inventors searched the human antibody data bases and found that two human antibodies, huFd138 HV and hu B-B10 LV, had the most identity to the original TNT-3 amino acid sequence of heavy chain and light chain, respectively. huFd138 HV had 81% homology of frameworks 1, 2, 3, and 4 to the mTNT-3 heavy chain sequence (see FIG. 1A); hu B-B10 LV had 74% homology of frameworks 1, 2, 3, and 4 to the mTNT-3 light chain sequence (see FIG. 1B). To reduce the effects of framework replacement on conformation of H-CDRs, three residues ($I^{48}$, $T^{74}$, and $Y^{95}$) were retained which are suspected to be important or due to close to CDR sequences on heavy chain frameworks. The original sequences of the six complementarity-determining regions (CDRs) of heavy and light chains were maintained and all other sequences were replaced by human sequences. Variable heavy and light chain sequences of EP candidates were combined with a $(GSSSS)_3$ linker to construct the EP/ScFv (see FIG. 1C). With further respect to FIGS. 1A-1B, an amino acid sequence alignment of murine TNT-3 and human TNT-3 template is shown. FIG. 1A illustrates alignment of murine TNT-3(mTNT-3), huFd138 HV, and EP heavy chains; FIG. 1B illustrates alignment of mTNT-3, hu B-B10 LV, and the EP light chain template. The numbering for each of the human templates is provided in the text. The frameworks and CDR sequences of the light and heavy chains based on the Kabat definition were labeled. * indicates residues replaced with human amino acids; # refers to murine residues maintained. FIG. 1C schematically shows HV and LV constructed into EP/ScFv with a $(GSSSS)_3$ linker. Notably, the EP/ScFv where six CDRs were simply grafted into the human the frameworks only showed a very weak reaction to crude DNA by phage-ELISA. This indicated that such replacement of frameworks had caused a big decrease of the EP/ScFv affinity.

Mutation of H-CDR3 of EP/ScFv and panning of its library against crude DNA: To improve the affinity of EP/ScFv, a site-specific random mutation on the H-CDR3 domain was conducted 11 primers, each of them containing a random mutated codon as shown in FIG. 2, were introduced into heavy chain by PCR one by one and resulted in 11 sub-libraries of mutated ScFv.

Figure 4:
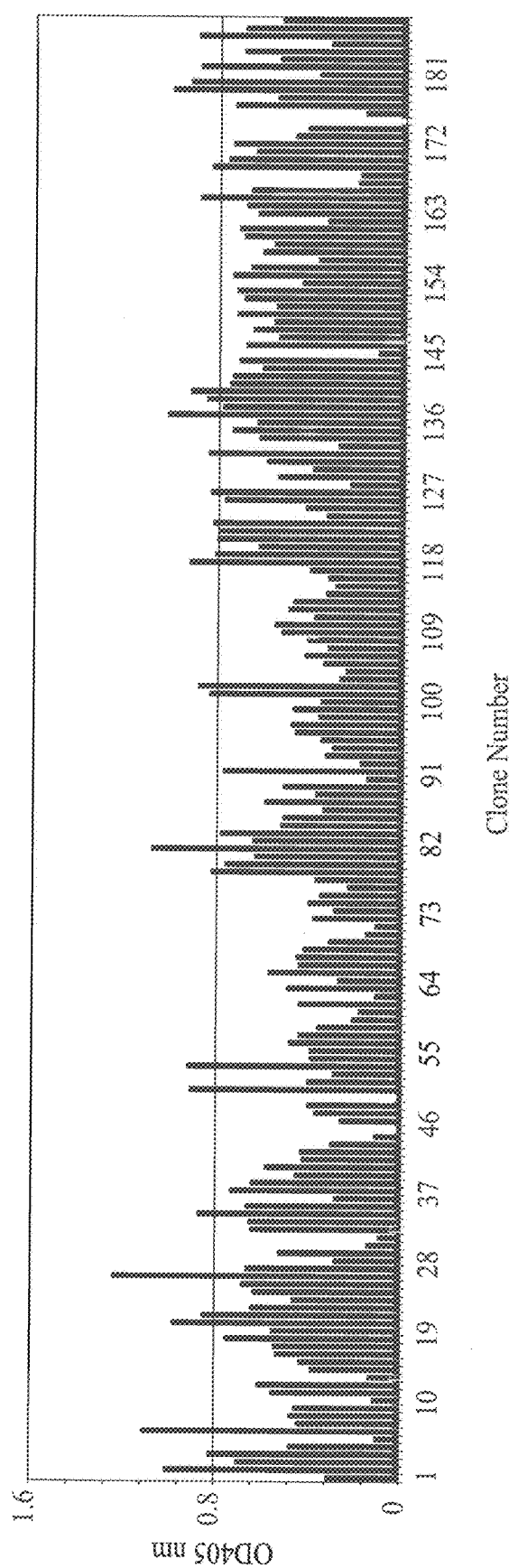
FIG. 4 is a plot illustrating clonal results for bound phagemids.

Eleven sub-libraries were equivalently mixed together, inserted into a digested lambda phage SurfZAP™ vector. EP ScFv was digested with SpeI and NotI were inserted into lambda phage SurfZAP vector and then excised into the pSurfscript SK(−) vector. This allowed EP/ScFv to be expressed as fusion proteins (ScFv/cpIII)), and made up a general library with 352 diversities. For the panning, this library was amplified to $10^{12}$ clones and rescued with M13 helper phage. After each round of panning, the library binding to crude DNA was detected by phage ELISA. An increasing binding was observed as panning times increased (FIG. 3: The phage displayed EP were selected and enriched by elution off DNA coated flasks. After each panning run, the supernatants were incubated in 96-well ELISA plates pre-coated with DNA. After washing, HRP-conjugated anti-M13 antibody was added and ABTS was used as substrate before reading the plates at 405 nm). Binding of library after the three round panning was 4 times more than that of original. More than 90% of the recovered clones after the four round panning were positive in DNA binding (FIG. 4: Phagemid particles were prepared from clones by PEG precipitation and resuspended in 1% Blotto/TBS Blocking buffer. $10^9$ cfu of each sample in 100 µl were added to crude DNA-coated ELISA plate wells. Removed unbound phagemid by washing with PBST. Bound Phagemid were detected with anti-M13 polyclonal antibody, followed by HRP-goat anti-rabbit IgG. Enzyme activity was measured using ABTS as substrate at 405 nm), which indicated that a high enrichment process had been done.

Figure 5:
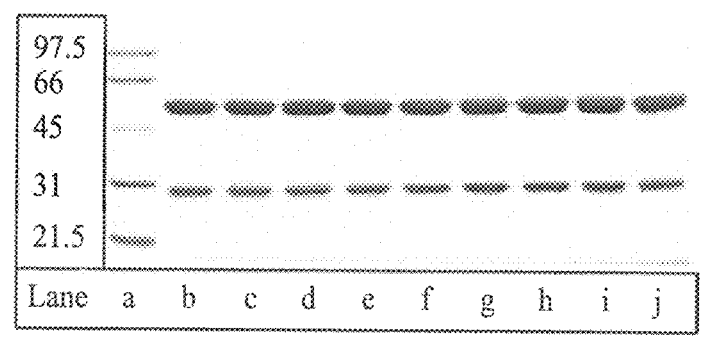
FIG. 5 is a photograph of an SDS gel with exemplary humanized IgG samples.

Construction, Expression, and Purification of EP IgG: Based on the screening results of phage ELISA from 4 round panning, 16 clones with a highest $OD_{405}$ values were selected and sequenced. Sequencing analysis showed that all the 16 clones contain 8 different nucleotide and amino acid sequences in H-CDR3. Determination of clones binding based on phage ELISA was limited by the purification and quantity of the phages that contained ScFv fusion proteins. Monovalent ScFv, which have 8 to 10 times lower affinities than the bivalent IgG would amplify this disadvantage. To further evaluate the difference among their affinities and to understand the relation between the binding and the site mutation on H-CDR3, as well as to restore the ability of the whole IgG antibody, all of the ScFv of 8 mutants were converted into corresponding IgG1 that were expressed with the Glutamine Synthetase Gene Amplification System. The highest yield clones were selected by a 24 hour ELISA assay. When the cell line was expanded in a 1-L bioreactor, their supernatants containing EP IgG1 were collected and purified stepwise by protein A affinity chromatography. About 10 µg/ml of EP IgG was obtained after purification. SDS-PAGE assay demonstrated that eight mutants of EP IgG1 (referred to herein as EP or huTNT IgG1s) had been properly assembled (FIG. 5: Lane (a) Low Range Markers (BioRad); (b) EP2; (c) EP7; (d) EP27.1; e. EP35.2; (f) EP51; g EP54; (h) EP102; (i) EP103; (j) chTNT-3). Two bands were exhibited at approximately 25 and 55 kD, corresponding to the molecular weights of EP IgG1 light chain and heavy chain, respectively.

Figure 6:
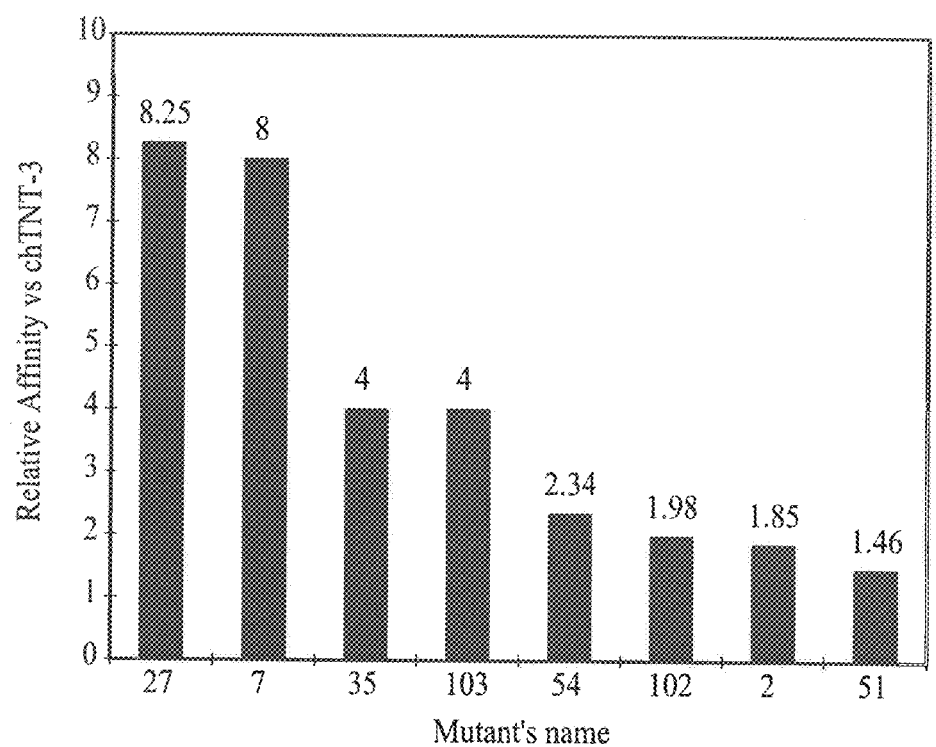
FIG. 6 is a graph depicting exemplary relative affinities of selected mutant antibody proteins that are EP27, EP7, EP35, EP103, EP54, EP102, and EP51

Assay of Affinities of EP Mutants and Characterization of mutation: To measure whether the binding activities of the EP IgG1 candidates had been improved, the inventors used ELISA to detect their binding activities against crude DNA. As can be readily seen from FIG. 6, eight candidates all have a significant improvement (from 1.45 to 8-fold) in affinity, compared with chTNT-3. Here, to measure the relative affinities of the EP mutants binding crude DNA, various concentrations of the purified EPIgG1 were tested by ELISA. The curves of the dose-dependent reactions were obtained and their concentration at 0.3 OD was determined by the best-fit line equation (purified chTNT-3 was used as standard). Their relative affinities were represented by the ratio of Conc.EP/Conc.chTNT-3 at 0.3 OD.

Combined analysis of affinities and mutation showed that two candidates of the highest affinity, EP/m7 and EP/27.1, obtained an about 8-fold improvement with the corresponding mutation of m7 Ile→His and 27.1 Gly→Arg (see Table 1). Another two of the clones, namely, EP/35.2 and EP/m103 (where 35.2 Tyr and m103 Arg changed to Thr and Leu, respectively), obtained a 4-fold increase in affinity. The remaining four clones, namely m54, m102, m2, and m51 (where the changes were m54 Arg→Leu, m102 Tyr→Arg, m2 Phe→Arg, m51 Val→Ser, respectively), also showed an increase in affinity ranging from 1.46 to 2.34 fold increase.

TABLE 1

| Mutant | Mutation | Frequency | Relative Binding to DNA |
|---|---|---|---|
| 2 | $^{107}$Phe→Arg | 1/16 | 1.85 |
| 7 | $^{101}$Ile→His | 2/16 | 8.0 |
| 27.1 | $^{102}$Gly→Arg | 3/16 | 8.25 |
| 35.2 | $^{109}$Tyr→Thr | 6/16 | 4.0 |
| 51 | $^{103}$Val→Ser | 1/16 | 1.46 |
| 54 | $^{104}$Arg→Thr | 1/16 | 2.34 |
| 102 | $^{109}$Tyr→Arg | 1/16 | 1.98 |
| 103 | $^{104}$Arg→Leu | 1/16 | 4.0 |

The analysis of amino acids properties on H-CDR3 of the mutants with improved affinity showed that positively charged amino acids such as Arg and His replaced existing residues in four of the mutants, while the other three mutants showed replacement with amino acids containing hydroxyl groups. These results implied that changes in the electrostatic or hydrogen bonding potential of residues contributed to the observed improvement in antibody binding to crude DNA. In one exceptional case (m103), the replacement of Arg with Leu also increased binding activity by four-fold.

Figure 7:
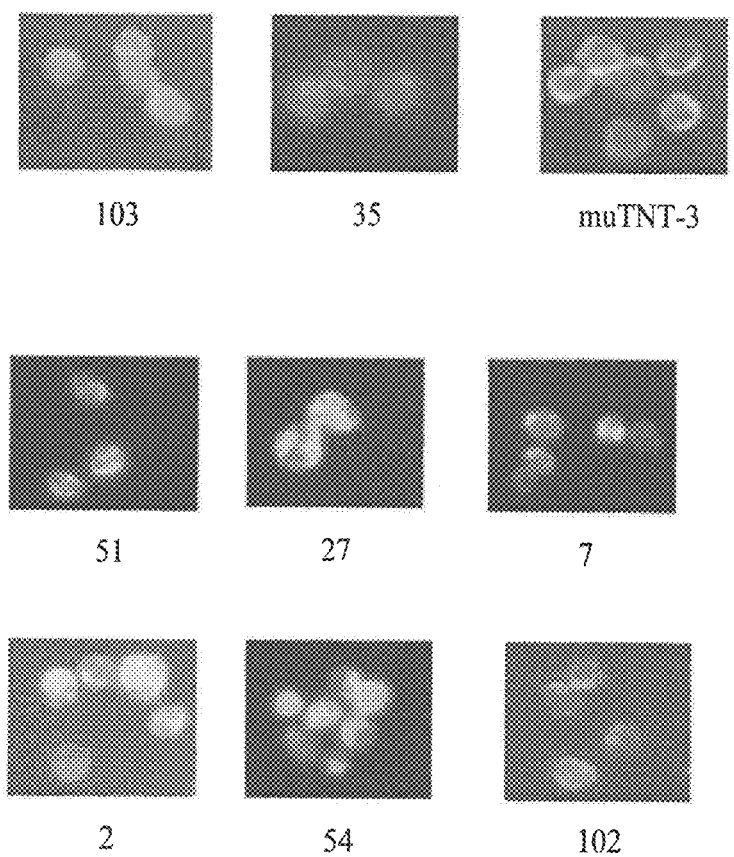
FIG. 7 shows various photomicrographs of immunostaining selected humanized antibodies according to the inventive subject matter.

Immunofluorescence Microscopy Studies: To observe the specificities of EP IgG candidates against antigen Raji cells, indirect immunofluorescence staining was performed. As shown in FIG. 7, EP IgG candidates all stained fixed Raji cells, giving a nuclear pattern of staining. EP2, 7, 27.1, 35.2, 51, 102, and 103 produced a prominent nuclear rim-staining similar to chTNT-3; only EP54 produced a homogenous nuclear staining pattern. No cytoplasmic or cell surface staining were noted with all preparations. Using an equivalent dose, the order of the strongest intensity of immunofluorescence staining was 51, 2, chTNT3>7, 27.1, 54, 102>103 and 35.2, which is quite differed from the results of their binding to crude DNA. EP7 and 27.1 which had the best affinity to crude DNA in ELISA studies did not show the corresponding reaction to fixed Raji cells, but EP51 and 2 which had a relative low affinity to crude DNA interestingly produced the strongest staining pattern.

Figure 8:
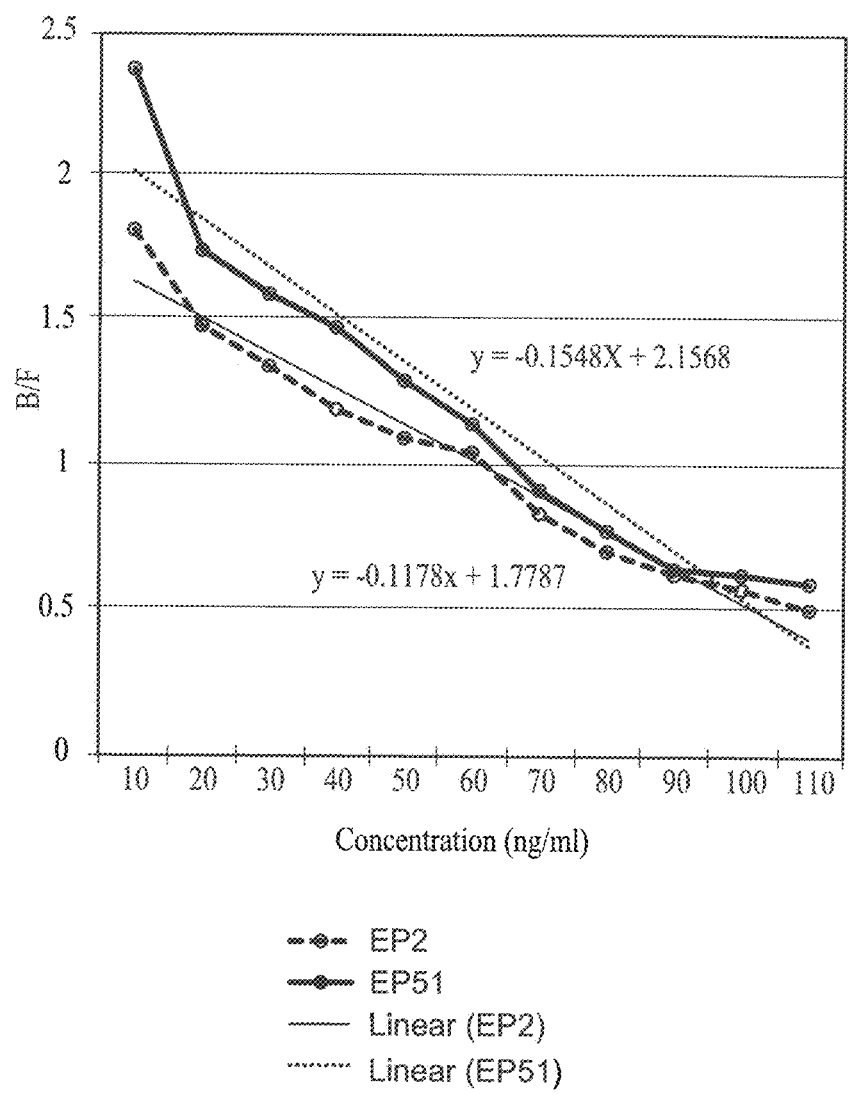
FIG. 8 is a graph showing affinity measurements for EP2 and EP51humanized antibodies.

Determination of the avidity constant (Ka) of EP by RIA: Based on the results of immunofluorescence staining, the avidity constants (Ka) of two EP IgG candidates (EP51 and EP2) which showed the best affinities to Raji cells were determined by RIA. Both EP IgG candidates were labeled with $^{125}$I and incubated with fixed Raji cells, and the bound radioactivity was used to calculate the avidity constant (FIG. 8). The avidity constants of EP51 and EP2 were $2.8 \times 10^9$ $M^{-1}$ and $2.1 \times 10^9$ $M^{-1}$, respectively. EP51 and EP2 showed a stronger affinity to antigen Raji cells than that of chTNT3 with an avidity constant $1.4 \times 10^9$ $M^{-1}$. The Ka values of EP51 and EP2 were consistent with the reactions to crude DNA and antigen Raji cells and were similar to chTNT-3.

Figure 9A:
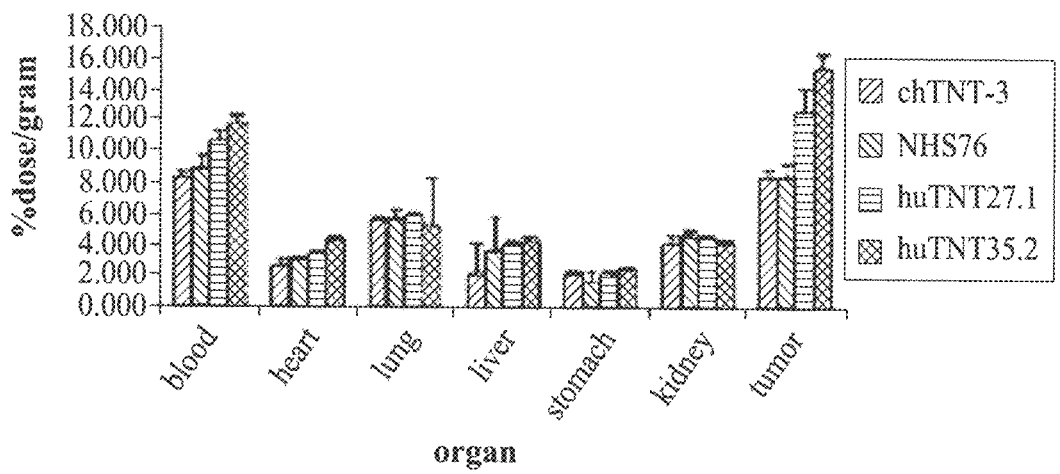
FIGS. 9A to 9D depict exemplary graphs for the biodistribution across various tissues and time points of various humanized antibody according to the inventive subject matter.
Figure 9B:
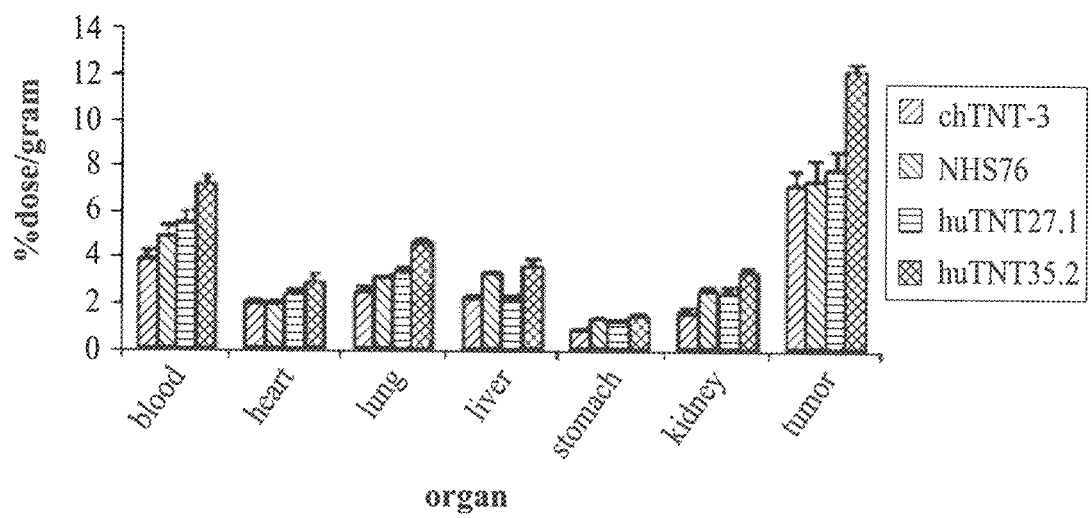
Figure 9C:
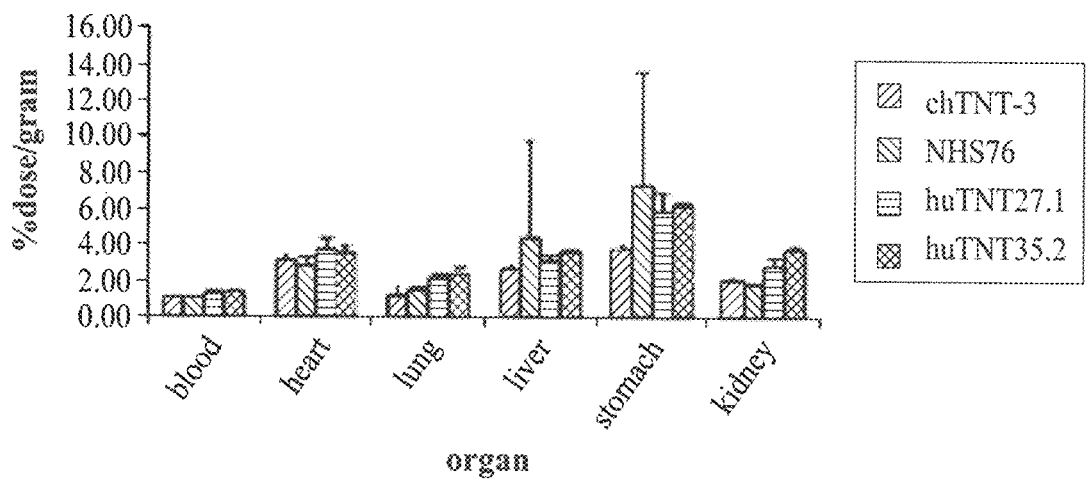
Figure 9D:
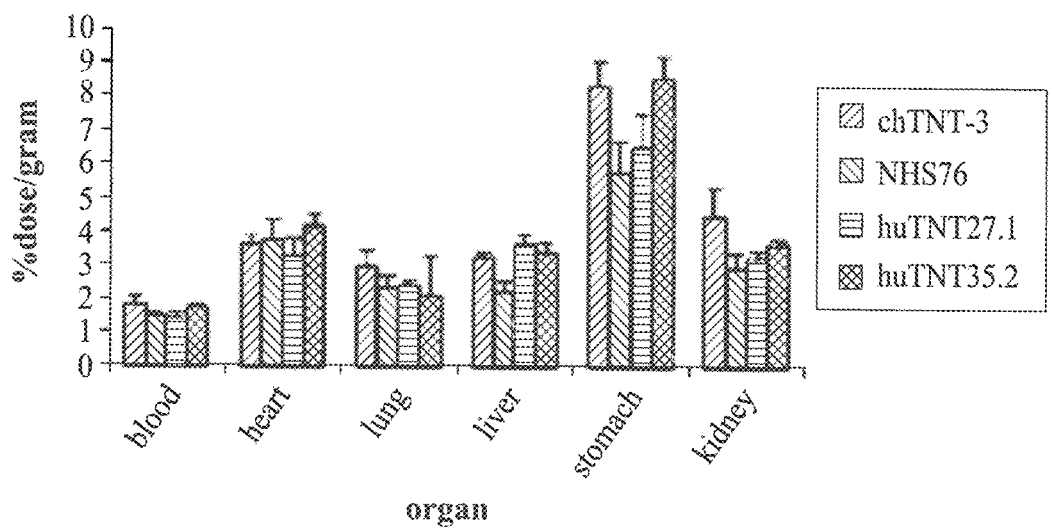

FIGS. 9A and 9C shows biodistribution studies in Colon 26-bearing mice using 1-125 labeled humanized antibodies after 3 days of biodistribution. FIGS. 9B and 9D show biodistribution after 7 days. Data are shown as injected dose/gram and normal organ to tumor ratios (n=5 mice) after different time points.

Figure 10:
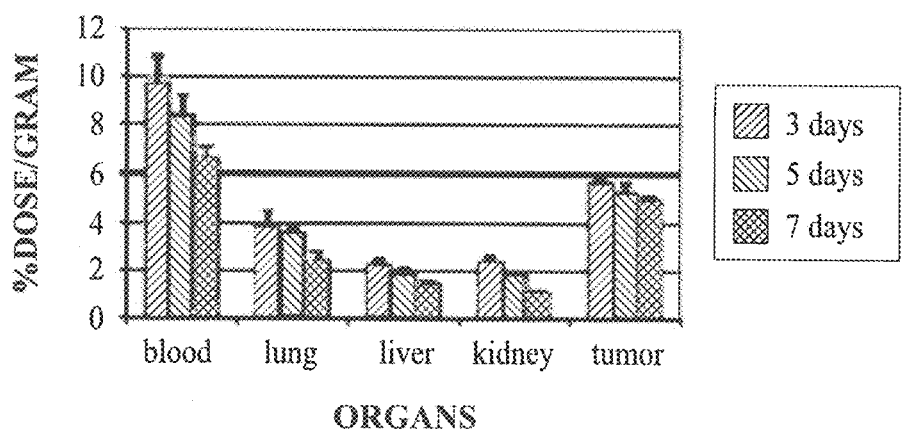
FIG. 10 depicts exemplary graphs for the biodistribution across various tissues of one humanized antibody according to the inventive subject matter without vascular penetration enhancement.

Biodistribution analysis of EP51 humanized antibody in LS174T colon cancer bearing nude mice showing specific and stable uptake in tumor at 3, 5, and 7 days (n=5) is shown in FIG. 10. By comparison, normal organs showed a decreasing uptake of label antibody indicative of clearance from blood pool and no off-target binding. Biodistribution analysis further showed that EP51 had the similar biodistribution characteristic to chTNT-3 as shown in Table 2.

TABLE 2

| | % Binding | | % Tumor Uptake in LS174T | | % Blood Uptake | |
|---|---|---|---|---|---|---|
| | Raji | CHO | 2 days | 5 days | 2 days | 5 days |
| huTNT3/m2 (EP2) | 65 | 35 | 2.69 | 1.33 | 3.45 | 2.46 |
| huTNT3/m7 (EP7) | 28 | 22 | ND | | | |
| huTNT3/m27 (EP27) | 36 | 23 | 4.0 | 2.14 | 7.67 | 4.84 |
| huTNT3/m35 (EP35) | 29 | 18 | 2.07 | 1.18 | 4.10 | 1.35 |
| huTNT3/m51 (EP51) | 70 | — | 5.90 | 4.97 | 10.7 | 8.5 |
| huTNT3/m54 (EP54) | 29 | 25 | 3.48 | 1.26 | 3.75 | 3.05 |
| huTNT3/m103 (EP103) | 39 | 29 | ND | | | |
| chTNT3 | 85 | 35 | 5.62 | 4.28 | 11.1 | 8.28 |

Percent tumor uptakes of EP51 in LS174T model, by 2 days and by 5 days, were respectively 5.90 and 4.97, comparable to chTNT3 (5.62 and 4.28). Percent blood uptakes were also very similar in amount. However, the percent tumor uptake of EP2 appeared much lower than that of chTNT-3 despite its 1.5 fold higher Ka than chTNT-3. By two and five days, the percent tumor uptakes of EP2 in the LS174T tumor model, were respectively 2.69 and 1.33, which are much lower than that of chTNT-3. Additional biodistribution studies shown in FIG. 9 for EP27.1 and EP35.2 subclones and FIG. 10 for EP51 demonstrated enhanced uptake in tumors, especially for EP51 compared to both chTNT-3 and the fully human TNT antibody NHS76. Impressively, EP51 had only a minor % injected dose/gram drop-off from 3 days to 7 days demonstrating that this human antibody was significantly retained by the tumor while uptake in normal tissues lost reactivity due to negative binding and clearance from the blood.

As can be seen from the above data, an initial humanized TNT-3 construct by framework replacement followed by six CDRs grafts only showed marginally detectable affinity, despite their humanized frameworks in HV and LV having identical sequences of 81% and 74% to that of mTNT3, respectively. This finding suggests that the humanization with a simple six CDR graft had changed the original conformation of CDRs. To restore affinity, site-specific random mutation of H-CDR3 was introduced by a set of primers. A library of EP ScFv with mutated H-CDR3 were displayed on lambda phage. After 4 rounds of selection against the crude DNA, eight mutants with a significant high affinity had been efficiently enriched, compared with the marginal detectable affinity of the initial humanized TNT-3.

ELISA studies of binding crude DNA showed that eight mutants all displayed much more affinity (from 1.45 to 8.25 fold) than that of the parent antibody, chTNT-3. Analysis of H-CDR-3 sequences showed that most of the mutations with high affinity had been replaced with positively charged amino acids such as Arg and His, or amino acids containing hydroxyl groups. These results suggested that changes in the electrostatic or hydrogen bonding potential of residues might contribute to the improvement in antibody binding to crude DNA. Interestingly, two mutants of the best affinity, EP7 and EP27.1, obtained an 8-fold improvement of affinity after the corresponding mutation of EP27.1 Gly→Arg and EP7 Ile→His. The potential role of amino acids Arg and His to binding DNA has been highlighted in both murine and human anti-DNA autoantibodies. Arg is the most important and versatile amino acid in DNA binding. It can form hydrogen bonds with base-paired guanine, as well as unpaired and base-paired cytosine and can fit into the major or the minor DNA groove through extensive interactions with the DNA sugar-phosphate backbone and with the flexible side chain facilitating the biding. This may partially explain the affinity improvement of EP27.1, EP2 and EP102 which have the same replacements with Arg. However, in one exceptional case, the replacement of Arg104 with Leu also increased binding activity by four-fold. Apparently, a simple accumulation of Arg replacement does not increase the affinity of binding DNA. The modification of Arg104→Leu may place Arg105 in a better position for its interaction with DNA.

Analysis of mutation sites on CDR3 of EP mutants from phage display and binding selection showed that residues 98 to 100, 105, 106, and 108 within H-CDR3 are most conserved, and that substitution mainly occurred at residues 101 to 104, 107, and 109. In contrast, the highest frequency of mutation was observed at residues 101, 104, 106, and 109. Complete conservative residues may take a role of contact directly to antigen and do more contribution to determine specificity. The inventors also found that original H-CDR3 contained two Arg residues (Arg104, Arg105) which is consistent anti-dsDNA autoantibodies bear at least one and in most cases two or three Arg in the H-CDR3. Arg104 could be substituted and Arg105 is conserved. The conserved Arg105 was in such a position which located at the center of H-CDR3 that it could effectively interact with DNA via hydrogen bonds and salt bridges. The conserved Arg105 combined with other conserved residues might play a critical role of DNA specific binding and residues of high mutation frequency may do more contribution to modulate the affinity of antibody.

Different order of reactive intensities of mutants in ELISA and immunofluorescence staining and their different pattern of distribution in Raji cells indicated that the epitope of some mutants against the same antigen had been changed or shifted due to mutation of their H-CDR3. This was tested using crude DNA for selection. The decision to use crude DNA for selection was based on the evidence that chTNT3, which was derived from the Raji cells nuclei, could largely bind single chain DNA. Though chTNT-3 showed a strong reaction to crude DNA, chTNT-3 may be more apt to bind complex form DNA in the nuclei. EP/m51, with about 2-fold of the affinities of chTNT-3 against crude DNA as well as Raji cells, showed similar biodistribution characteristics in vivo to chTNT-3. EP/m51's % tumor uptake also tended to be better than that of chTNT-3. All this suggested that the humanization of mTNT-3 by CDRs grafting, combined with mutation, was successful and a humanized EP antibody with an improved affinity had been obtained.

Therefore, it should be appreciated that (1) mutation on H-CDR3 is an efficient method to improve the affinity of a humanized antibody; (2) one humanized mutant (EP51) with the same specificity and higher affinity had been obtained, which showed a good biodistribution profile in vivo required for clinical potential; (3) the results illustrate that humanized antibodies against different epitopes of the same antigen can be obtained at the same time, and the risk of specificity shift of humanized antibody due to mutation of CDR3 can be avoided or controlled by selecting a suitable antigen; and (4) the information obtained by studying specificities and affinities of EP mutants widen the knowledge of chTNT3 binding to nuclear antigens and was useful in improving the EP affinities and specificities. Finally, biodistribution studies in tumor-bearing mice showed that one candidate, EP35.2, had high and superior uptake in tumor with good retention after 7 days of study and appears superior in vivo than chTNT-3 or fully human NHS76 in this experimental tumor model.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

The invention claimed is:

1. A hybrid molecule comprising a binding portion of an antibody coupled to an immune stimulatory agent, wherein the binding portion comprises a heavy chain (VH) with three complementarity determining regions (H-CDRs) and a light chain (VL) with three CDRs (L-CDRs), wherein H-CDR1 comprises SEQ ID NO: 1, H-CDR2 comprises SEQ ID NO:2, H-CDR3 comprises a sequence selected from the group consisting of SEQ ID NOs:27-34, L-CDR1 comprises SEQ ID NO:4, L-CDR2 comprises SEQ ID NO:5, and L-CDR3 comprises SEQ ID NO:6.

2. The hybrid molecule of claim 1, wherein H-CDR3 comprises SEQ ID NO:29.

3. The hybrid molecule of claim 1, wherein the VH sequence has at least 90% sequence identity to SEQ ID NO:7.

4. The hybrid molecule of claim 1, wherein the VL sequence has at least 90% sequence identity to SEQ ID NO:8.

5. The hybrid molecule of claim 1, wherein the VH sequence has at least 96% sequence identity to SEQ ID NO:7.

6. The hybrid molecule of claim 1, wherein the VL sequence has at least 96% sequence identity to SEQ ID NO:8.

7. The hybrid molecule of claim 1, wherein the binding portion comprises an Fab fragment, an F(ab')2 fragment, an Fab2 fragment, or an scFv.

8. The hybrid molecule of claim 1, wherein the immune stimulatory agent comprises a cytokine, wherein the cytokine is selected from a list comprising IL-2, IL-12, IL15, IL-15 superagonists, and TLR agonists.

9. The hybrid molecule of claim 1, wherein the immune stimulatory agent is an IL-15 superagonist.

10. The hybrid molecule of claim 1, wherein the immune stimulatory agent is IL-12.

11. A pharmaceutical composition comprising a pharmaceutically acceptable carrier and the hybrid molecule of claim 1.

12. A method of targeting a necrotic cell, the method comprising contacting the necrotic cell with the hybrid molecule of claim 1.

13. The method of claim 12, wherein the hybrid molecule contacts the necrotic cell in vivo.

14. The method of claim 12, wherein the hybrid molecule contacts the necrotic cell ex vivo.

15. A method of delivering an immune stimulatory agent to a tumor microenvironment containing necrotic tumor cells, the method comprising contacting the necrotic tumor cells in the microenvironment with the hybrid molecule of claim 1 under conditions that allow the binding domain to bind to a nuclear target in the necrotic cell.

16. The method of claim 15, wherein the tumor is a solid tumor.

17. The method of claim 15, further comprising a step of administering a vasculature permeability enhancing agent.

* * * * *